United States Patent

Schromm et al.

[11] 4,083,980
[45] Apr. 11, 1978

[54] DERIVATIVES OF QUINAZOLONE

[75] Inventors: Kurt Schromm, Ingelheim; Anton Mentrup, Mainz-Kastel; Ernst-Otto Renth; Armin Fügner, both of Ingelheim, all of Germany

[73] Assignee: Boehringer Ingelheim GmbH, Ingelheim am Rhine, Germany

[21] Appl. No.: 750,725

[22] Filed: Dec. 15, 1976

[30] Foreign Application Priority Data
Dec. 19, 1975 Germany .................... 2557425

[51] Int. Cl.² .................... A61K 31/505; C07D 487/04
[52] U.S. Cl. .................... 424/251; 260/251 A; 260/251 QA; 260/256.4 F
[58] Field of Search .................... 260/256.4 F; 424/251

[56] References Cited
U.S. PATENT DOCUMENTS 3,598,823  8/1971  Hardtmann .................... 260/256.4 F
3,833,588  9/1974  Hardtmann .................... 260/256.4 F Primary Examiner—Richard J. Gallagher
Assistant Examiner—James H. Turnipseed
Attorney, Agent, or Firm—Hammond & Littell

[57] ABSTRACT

Compounds of the formula

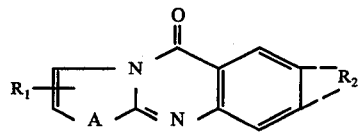

wherein
A is —CH=CH—, —CH=N— or —S—,
$R_1$ is hydrogen, lower alkyl, lower alkoxy, amino, acetylamino, cyano, tetrazol-5-yl, —$COR_3$ or a fused benzene ring,
where $R_3$ is lower alkoxy, amino, hydroxyamino, tetrazol-5-yl-amino or, when $R_2$ is other than hydrogen, also hydroxyl, and
$R_2$ is cyano, tetrazol-5-yl, —$COR_4$ or, when $R_1$ is cyano, tetrazol-5-yl or —$COR_3$, also hydrogen, lower alkyl, lower alkoxy, amino, acetylamino or a fused benzene ring,
where $R_4$ is lower alkoxy, amino, hydroxyl, hydroxyamino or tetrazol-5-yl-amino;

non-toxic, pharmacologically acceptable acid addition salts thereof; and, when $R_3$ and/or $R_4$ are hydroxyl, non-toxic, pharmacologically acceptable salts thereof formed with an inorganic or organic base. The compounds as well as their salts are useful primarily as anti-allergics.

7 Claims, No Drawings

DERIVATIVES OF QUINAZOLONE

This invention relates to novel derivatives of quinazolone and salts thereof, as well as to various methods of preparing these compounds, pharmaceutical compositions containing them as active ingredients, and methods of using them as antiallergics.

More particularly, the present invention relates to a novel class of quinazolone derivatives represented by the formula

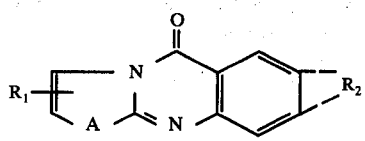

wherein
A is —CH=CH—, —CH=N— or —S—,
$R_1$ is hydrogen, lower alkyl, lower alkoxy, amino, acetylamino, cyano, tetrazol-5-yl, —COR$_3$ or a fused benzene ring,
  where $R_3$ is lower alkoxy, amino, hydroxyamino, tetrazol-5-yl-amino or, when $R_2$ is other than hydrogen, also hydroxyl, and
$R_2$ is cyano, tetrazol-5-yl, —COR$_4$ or, when $R_1$ is cyano, tetrazol-5-yl or —COR$_3$, also hydrogen, lower alkyl, lower alkoxy, amino, acetylamino or a fused benzene ring,
  where $R_4$ is lower alkoxy, amino, hydroxyl, hydroxyamino or tetrazol-5-yl-amino;
non-toxic, pharmacologically acceptable acid addition salts thereof; and, when $R_3$ and/or $R_4$ are hydroxyl, non-toxic, pharmacologically acceptable salts thereof formed with an inorganic or organic base.

The terms "lower alkyl" and "lower alkoxy", as used herein, are intended to designate alkyl and alkoxy radicals of 1 to 6 carbon atoms, and those of 1 to 2 carbon atoms are preferred.

A preferred sub-genus thereunder is constituted by compounds of the formula

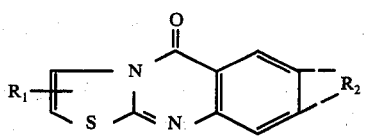

wherein
$R_1$ is hydrogen, a fused benzene ring, tetrazol-5-yl or —COR$_3$,
  where $R_3$ is hydroxyl, hydroxyamino or tetrazol-5-yl-amino, and
$R_2$ is hydrogen, a fused benzene ring, tetrazol-5-yl or —COR$_4$,
  where $R_4$ is hydroxyl, hydroxyamino or tetrazol-5-yl-amino;
non-toxic, pharmacologically acceptable acid addition salts thereof; and, when $R_3$ and/or $R_4$ are hydroxyl, non-toxic, pharmacologically acceptable salts thereof formed with an inorganic or organic base.

Finally, an expecially preferred sub-genus thereunder is constituted by compounds of the formula

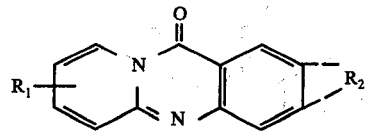

wherein $R_1$ and $R_2$ have the meanings defined in conjunction with formula Ia above; non-toxic, pharmacologically acceptable acid addition salts thereof; and, when $R_3$ and/or $R_4$ are hydroxyl, non-toxic, pharmacologically acceptable salts thereof formed with an inorganic or organic base.

The compounds embraced by formula I may be prepared by various methods involving known chemical synthesis principles, among which the following are preferred:

Method A

For the preparation of a compound of the formula I in which $R_1$ is hydrogen, lower alkyl, lower alkoxy, acetylamino, carboxyl, tetrazol-5-yl or a fused benzene ring, and $R_2$ is carboxyl, tetrazol-5-yl or, when $R_1$ is carboxyl or tetrazol-5-yl, also lower alkyl, lower alkoxy, acetyl-amino or a fused benzene ring, by reacting a compound of the formula

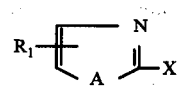

wherein
$R_1$ is hydrogen, lower alkyl, lower alkoxy, acetylamino, carboxyl, tetrazol-5-yl or a fused benzene ring,
A is —CH=CH—, —CH=N— or —S—, and
X is halogen, preferably fluorine, chlorine or bromine,
with a compound of the formula

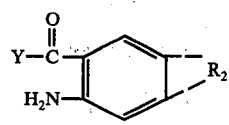

wherein
$R_2$ is carboxyl, tetrazol-5-yl or, when $R_1$ in formula II is carboxyl or tetrazol-5-yl, also lower alkyl, lower alkoxy, acetylamino or a fused benzene ring, and
Y is lower alkoxy, at elevated temperatures, preferably in the range of about 120° to 160° C. The reaction may be carried out in the absence of a solvent or also in a high-boiling-point solvent, such as dimethylformamide or sulfolane, and advantageously in the presence of an acid acceptor. An excess of the reactant of the formula III may serve as an acid acceptor.

The starting compounds of the formulas II and III are known compounds and can be obtained by conventional methods.

Method B

For the preparation of a compound of the formula I in which A is —CH=CH— or —CH=N—, $R_1$ is hydrogen, lower alkoxy or carboxyl, and $R_2$ is carboxyl or, when $R_1$ is carboxyl, also lower alkoxy, by oxidizing a compound of the formula

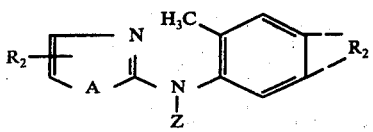

wherein
A is —CH=CH— or —CH=N—,
$R_1$ is hydrogen, lower alkoxy or carboxyl,
$R_2$ is carboxyl or, when $R_1$ is carboxyl, also lower alkoxy, and
Z is acyl, especially lower alkanoyl,
with a strong oxidizing agent at elevated temperatures, followed by acidification of the reaction mixture. For example, the oxidation can be effected with an aqueous solution of potassium permanganate buffered with magnesium sulfate. Examples of acids which can be used for subsequent acidification are mineral acids, such as hydrochloric acid, or also organic acids, such as acetic acid.

The starting compounds of the formula IV can be prepared by conventional methods. If $R_1$ and/or $R_2$ in formula IV are carboxyl, this substituent can also be formed in situ from the corresponding methyl-substituted compound or from other correspondingly substituted compound which are converted into the carboxyl-substituted compounds under the reaction conditions.

Method C

By converting substituents Q and/or R in a compound of the formula

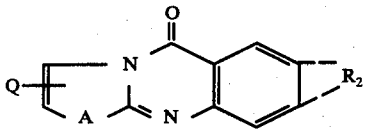

wherein
Q has the meanings defined for $R_1$ in formula I or is a precursor thereof, and
R has the meanings defined for $R_2$ in formula I or is a precursor thereof,
provided at least one of Q and R is a precursor of $R_1$ and $R_2$, respectively, into $R_1$ and/or $R_2$.

The conversion can be effected by conventional methods. For example, amides, esters and hydroxamic acids can be obtained from the corresponding carboxylic acid chlorides by reaction with ammonia or aminotetrazole, with a corresponding lower alkanol or with hydroxylamine, respectively; the tetrazol-5-yl-substituted compounds can be obtained by reacting the corresponding nitriles with sodium azide; the cyano-substituted compounds can be obtained from the corresponding carbamoyl-substituted compounds; the carboxyl-substituted compounds can be obtained by hydrolysis of the corresponding esters or amides, or also by oxidation of the corresponding methyl-substituted compounds with potassium permanganate, for instance; and the amino-substituted compounds can be obtained by acid or alkaline hydrolysis of the corresponding acylamino-substituted compounds.

The starting compounds of the formula V may be prepared either by methods A or B, or by other known methods.

The end products of the formula I obtained by methods A – C form acid addition salts with inorganic or organic acids or, when they contain free carboxyl groups, also salts with inorganic or organic bases. These salts may be prepared by conventional methods. Conversely, if a salt of a compound of the formula I is obtained as the end product, the corresponding free base or acid of the formula I may be liberated therefrom by conventional methods.

The following examples illustrate the present invention and will enable others skilled in the art to understand it more completely. It should be understood, however, that the invention is not limited solely to the particular examples given below.

EXAMPLE 1

Ethyl 5-oxo-5-H-thiazolo[2,3-b]quinazoline-7-carboxylate by method A

A mixture consisting of 2.4 gm of 2-chloro-thiazole and 5.6 gm of ethyl 4-amino-isophthalate was heated for eight hours at 150° C on an oil bath. Thereafter, the resulting dark brown oil was refluxed with 10 ml of acetonitrile for one hour, the reaction mixture was then thoroughly cooled, and the crystals formed thereby were collected by suction filtration and recrystallized from a little methanol. The compound of the formula

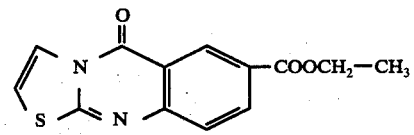

having a melting point of 148°–155° C (faintly yellow needles) was obtained.

Elemental analysis: $C_{13}H_{10}N_2SO_3$ Calculated: C-56.93%; H-3.65%; N-10.22%; S-11.68% Found: C-56.87%; H-3.82%; N-10.21%; S-11.82%

EXAMPLE 2

Ethyl 8-oxo-8-H-isoquino[1,2-b]quinazoline-10-carboxylate by method A 4.97 gm of 1-chloro-isoquinoline were admixed with 14.4 gm of ethyl 4-amino-isophthalate, and the mixture was heated slowly to 150° C; the molten mixture solidified after about 45 minutes, whereupon 50 ml of ethanol were added thereto, and the resulting mixture was refluxed for one hour. Thereafter, the reaction solution was cooled, and the crystals formed thereby were collected by suction filtration, yielding the hydrochloride of ethyl 8-oxo-8-H-isoquino[1,2-b] quinazoline-10-carboxylate. The free base was liberated from the hydrochloride by dissolving the latter in water, adding the calculated amount of sodium bicarbonate, and extracting the mixture with chloroform. The chloroform extract was evaporated and the residue was purified on a silicagel column, yielding lemon-yellow crystals having a melting point of 205°–210° C which were identified to be the compound of the formula

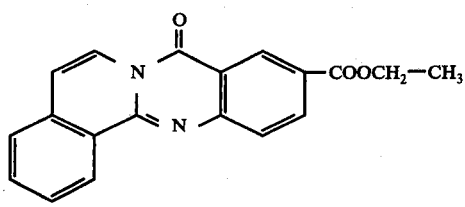

Elemental analysis: $C_{19}H_{14}N_2O_3$ Calculated: C-71.70%; H-4.40%; N-8.81% Found: C-71.58%; H-4.40%; N-8.68%

EXAMPLE 3

Using a procedure analogous to that described in Example 2, ethyl-12-oxo-12-H-quino[2,1-b]quinazoline-10-carboxylate, m.p. 157°–163° C, of the formula

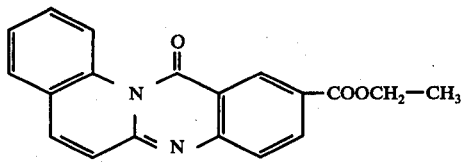

was obtained from 4.1 gm of 2-chloroquinoline and 11.9 gm of ethyl 4-amino-isophthalate.

Elemental analysis: $C_{19}H_{14}N_2O_3$ Calculated: C-71.70%; H-4.40%; N-8.81%; O-15.09% Found: C-71.70%; H-4.17%; N-8.67%; O-15.95%

EXAMPLE 4

11-Oxo-11-H-2-methyl-pyrido[2,1-b]quinazoline-8-carboxylic acid by method A

A mixture consisting of 4.37 gm of 6-chloro-nicotinic acid and 4.53 gm of 5-methyl-anthranilic acid was heated to 150° C. The molten reaction mixture solidified after a few minutes, whereupon it was boiled with a 5-fold amount of concentrated hydrochloric acid. The resulting solution was cooled, then suction-filtered, and the filter cake was washed with water and acetonitrile, yielding the hydrochloride of 11-oxo-11-H-2-methyl-pyrido[2,1-b]quinazoline-8-carboxylic acid. The hydrochloride was suspended in water and caused to go into solution by addition of the calculated amount of sodium bicarbonate to form the sodium salt of the acid. Upon acidification of the solution with acetic acid, the free acid of the formula

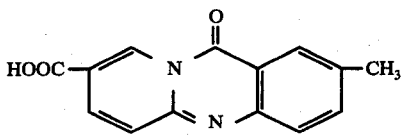

precipitated out.

Elemental analysis: $C_{14}H_{10}N_2O_3$ Calculated: C-66.14%; H-3.94%; N-11.02% Found: C-66.19%; H-4.09%; N-11.11%

EXAMPLE 5

13-Oxo-13-H-benzo[g]pyrido[2,1-b]quinazoline-10-carboxylic acid and its hydrochloride by method A A mixture consisting of 1.32 gm of 6-chloro-nicotinic acid and 1.8 gm of ethyl 3-amino-2-naphthoate was heated to 160° C. The molten mixture solidified after a short time, whereupon it was boiled with 100 ml of ethanol. The crystalline substance formed thereby was heated for two hours with aqueous 20% sodium hydroxide, and then ethanol was added, the resulting solution was filtered, the filtrate was acidified with glacial acetic acid, and the crystals formed thereby was collected by suction filtration, yielding the free acid named in the heading. Treatment of the free acid with concentrated hydrochloric acid yielded the yellow crystalline hydrochloride of the formula

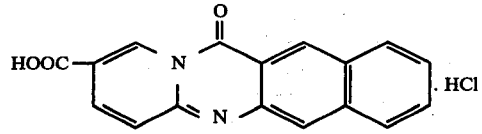

Elemental analysis: $C_{17}H_{10}N_2O_3$ . HCl Calculated: C-62.48%; H-3.37%; N-8.58%; Cl-10.87% Found: C-62.62%; H-3.50%; N-8.33%; Cl-10.02%

EXAMPLE 6

Using a procedure analogous to that described in Example 5, the hydrochloride of 11-oxo-11-H-2-methoxy-pyrido [2,1-b]quinazoline-8-carboxylic acid, m.p. >300° C, of the formula

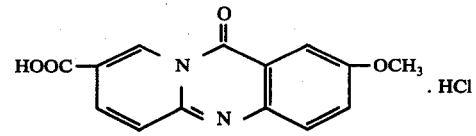

was obtained from 1.58 gm of 6-chloro-nicotinic acid and 3.9 gm of ethyl 5-methoxy-anthranilate.

Elemental analysis: $C_{14}H_{10}N_2O_4$ . HCl Calculated: C-54.81%; H-3.59%; N-9.14%; Cl-11.58%

Found: C-54.78%; H-3.66%; N-8.94%; Cl-11.56%

In like manner, using procedures analogous to those described in Examples 1 to 6, the following additional compounds of the formula I were prepared: 11-oxo-11-H-pyrido[2,1-b]quinazoline-8-carboxylic acid, 6-oxo-6-H-pyrimido[2,1-b]quinazoline-8-carboxylic acid, 12-oxo-12-H-quino[2,1-b]quinazoline-10-carboxylic acid, and 11-oxo-11-H-pyrido[2,1-b]quinazoline-3-carboxylic acid.

EXAMPLE 7

11-Oxo-11-H-pyrido[2,1-b]quinazoline-2-carboxylic acid by method B 60 gm of pyridyl(2)-N-(2,4-dimethyl-phenyl)-acetamide were oxidized with 218 gm of potassium permanganate and 75.5 gm of magnesium sulfate in 2 liters of water at a temperature of 40°–90° C. The manganese dioxide which had separated out was suction-filtered off, the filtrate was acidified with acetic acid, and the substance which slowly crystallized out of the acidic solution was collected by suction filtration and then stirred for one hour at 60°–70° C with a fivefold amount of concentrated hydrochloric acid. Thereafter, the solution was diluted with ten times its volume of water, whereupon the reaction product gradually precipitated out. The precipitate was collected and washed with water and acetonitrile, yielding the compound of the formula

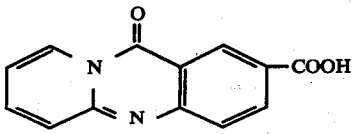

Elemental analysis: $C_{13}H_8H_2O_3$ Calculated: C-65.00%; H-3.33%; H-11.67% Found: C-64.95%; H-3.46%; H-11.58%

The starting compound, pyridyl(2)-N-(2,4-dimethyl-phenyl)-acetamide, was prepared by condensation of equimolar amounts of 2,4-dimethyl-aniline and 2-bromo-pyridine at 160°-180° C to form 2,4-dimethyl-N-pyridyl(2)-aniline which, after purification via its fumarate, had a melting point of 65°-68° C, and heating the intermediate with acetic acid anhydride.

(a) The sodium salt of 11-oxo-11-H-pyrido[2,1-b]quinazoline-2-carboxylic acid was obtained by dissolving the acid in water, adding the calculated amount of sodium bicarbonate, and precipitating the salt with ethanol.

(b) The ethanolamine salt was obtained by suspending 1.2 gm of the free acid in 3 ml of water, adding 0.31 ml of ethanolamine thereto, and precipitating the salt with acetonitrile.

Elemental analysis: $C_{15}H_{15}N_3O_4 \cdot H_2O$ Calculated: C-56.43%; H-5.33%; N-13.17% Found: C-57.25%; H-4.96%; N-13.46%

(c) The triethanolamine salt, which decomposed above 200° C, was obtained by suspending 2.4 gm of the free acid in 20 ml of acetonitrile, and adding 3.6 gm of about 85% triethanolamine to the suspension.

Elemental analysis: $C_{19}H_{23}N_3O_6$ Calculated: C-58.61%; H-5.91%; N-10.80% Found: C-58.80%; H-5.72%; N-11.00%

EXAMPLE 8

Using a procedure analogous to that described in Example 7, 11-oxo-11-H-pyrido[2,1-b]quinazoline-3-carboxylic acid of the formula

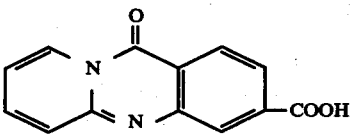

was prepared by reacting 2,5-dimethyl-aniline with 2-bromopyridine to form the intermediate N-pyridyl(2)-N-(2,5-dimethyl-phenyl)-acetamide, and oxidizing the latter with potassium permanganate.

Elemenetal analysis: $C_{13}H_8N_2O_3$ Calculated: C-65.50%; H-3.33%; N-11.67% Found: C-65.24%; H-3.21%; N-11.79%

EXAMPLE 9

6-Oxo-6-H-pyrimido[2,1-b]quinazoline-8-carboxylic acid hydrochloride by method B A mixture consisting of 9.5 gm of 2-amino-pyridine, 18.5 gm of 4-bromo-m-xylene, 13.8 gm of potassium carbonate and 0.5 gm of copper powder was heated at 180° C for five hours. Thereafter, the reaction mixture was diluted with water, the aqueous mixture was extracted with ether, and the ethereal extract solution was evaporated, leaving 2,4-dimethyl-N-pyrimidyl(2)-aniline, m.p. 95°-99° C.

In analogy to Example 7, the intermediate thus obtained was acetylated, oxidized with potassium permanganate, cyclized, and the end product was isolated as the hydrochloride of the formula

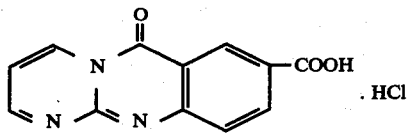

Elemental analysis: $C_{12}H_7N_3O_3 \cdot HCl$ Calculated: C-51.89%; H-2.88%; N-15.33% Found: C-51.89%; H-3.03%; N-15.87%

(a) The sodium salt of the acid was obtained by dissolving the hydrochloride in water, adding 2 mol-equivalents of sodium bicarbonate, and precipitating the salt with ethanol.

EXAMPLE 10

11-Oxo-11-H-2-methoxypyrido[2,1-b]quinazoline-8-carboxylic acid of the formula

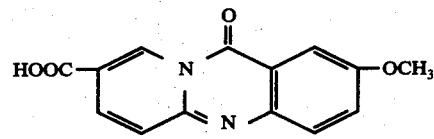

and its salts were prepared in analogy to Examples 7 to 9.

EXAMPLE 11

8-Acetamido-11-H-11-oxo-pyrido[2,1-b]quinazoline-2-carboxylic acid by method B

A mixture consisting of 9.5 gm of N-[5-diacetylamino-pyridyl-(2)]-N-(2,4-dimethyl-phenyl)-acetamide, 26.5 gm of potassium permanganate, 3.5 gm of magnesium sulfate and a mixture of water and butanol (2:1) was stirred for 4 hours at 80°-85° C. Thereafter, the reaction mixture was suction-filtered, the filtrate was evaporated, and the residue was heated for one hour with dilute acetic acid. During that time a crystalline substance gradually separated out, which was collected by suction filtration and washed with acetonitrile and ether, yielding the compound of the formula

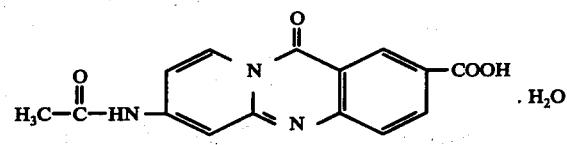

Elemental analysis: $C_{15}H_{11}H_3O_4 \cdot H_2O$ Calculated: C-57.14%; H-4.76%; N-13.33%; $H_2O$-5.7% Found: C-57.68%; H-4.69%; N-13.15%; $H_2O$-4.1%

EXAMPLE 12

Methyl 11-oxo-11-H-pyrido[2,1-b]quinazoline-2-carboxylate 6.2 gm of 11-oxo-11-H-pyrido[2,1-b]quinazoline-2-carboxylic acid (for preparation see Example 7) were refluxed with ten times its amount of thionyl chloride for one hour. Thereafter, the insoluble carboxylic acid chloride which had formed was collected by suction filtration and refluxed with from ten to twenty times its amount of methanol until it went completely into solution. Upon cooling, the hydrochloride with one mol of methanol of crystallization (decomp. >254° C) of the formula

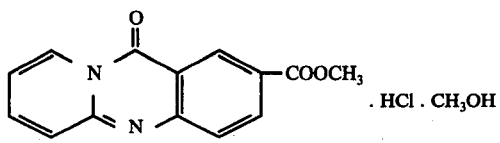

crystallized out.

Elemental analysis: $C_{14}H_{10}N_2O_3 \cdot HCl \cdot CH_3OH$ Calculated: C-55.81%; H-4.65%; N-8.68%; Cl-11.01% Found: C-55.53%; H-4.35%; N-8.82%; Cl-11.29%

EXAMPLE 13

11-Oxo-11-H-pyrido[2,1-b]quinazoline-2-[N-(1-H-tetrazole-5-yl)]-carboxamide by method C 5.53 gm of 11-oxo-11-H-pyrido[2,1-b]quinazoline-2-carboxylic acid chloride hydrochloride, prepared as in Example 12, were introduced into a solution of 2.1 gm of aminotetrazole hydrate and 6.1 gm of triethylamine in 200 ml of dimethylformamide at 0°– 10° C, and the mixture was stirred for three hours. Thereafter, acetic acid was added to the reaction mixture until it was acidic, and the precipitate formed thereby was collected by suction filtration, yielding the compound of the formula

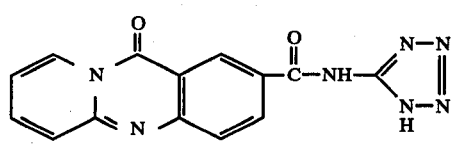

having a decomposition point of 330° C.

Elemental analysis: $C_{14}H_9N_7O_2$ Calculated: C-54.72%; H-2.93%; N-31.92% Found: C-54.93%; H-3.17%; N-31.63%

EXAMPLE 14

11-Oxo-11-H-pyrido[2,1-b]quinazoline-2-carboxamide by method C 10 gm of 11-oxo-11-H-pyrido[2,1-b]quinazoline-2-carboxylic acid chloride, prepared as in Example 12, were introduced into a mixture consisting of 200 ml of dioxane and 50 ml of concentrated ammonia, and the resulting mixture was stirred for 5 hours at room temperature. Thereafter, the reaction mixture was acidified with dilute acetic acid, and the crystals precipitated thereby were collected by suction filtration, yielding the compound of the formula

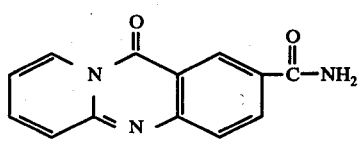

Elemental analysis: $C_{13}H_9N_3O_2$ Calculated: C-65.27%; H-3.77%; N-17.57% Found: C-65.00%; H-3.65%; N-17.38%

EXAMPLE 15

2-Cyano-11-oxo-11-H-pyrido[2,1-b]quinazoline by method C 4.8 gm of 11-oxo-11-H-pyrido[2,1-b]quinazoline-2-carboxamide (see Example 14) were suspended in 150 ml of dimethylformamide, the suspension was heated to 50°-60° C, and 3.3 ml of thionyl chloride were added dropwise to the hot suspension. After all of the thionyl chloride had been added, the mixture was stirred for 10 hours at 90°-100° C. Thereafter, the reaction mixture was neutralized with a dilute aqueous sodium carbonate solution, and the precipitate was collected by suction filtration and recrystallized from dimethylformamide, yielding the compound of the formula

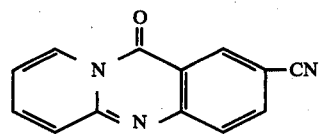

which had a decomposition point of 268°-271° C.

Elemental analysis: $C_{13}H_7N_3O$ Calculated: C-70.59%; H-3.17%; N-19.00% Found: C-70.42%; H-3.04%; N-19.00%

EXAMPLE 16

11-Oxo-11-H-pyrido[2,1-b]-2-(1H-tetrazol-5-yl)-quinazoline by method C

A mixture consisting of 5.2 gm of 2-cyano-11-oxo-11-H-pyrido[2,1-b]quinazoline (Example 15), 1.8 gm of sodium azide, 1.5 gm of ammonium chloride and 60 ml of dimethylformamide was heated for 10 hours at 90°-110° C. Thereafter, the reaction mixture was acidified with dilute acetic acid, and the precipitate formed thereby was collected by suction filtration, yielding the compound of the formula

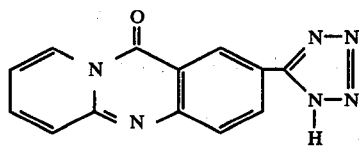

Elemental analysis: $C_{13}H_8N_6O$ Calculated: C-59.09%; H-3.03%; N-31.82% Found: C-58.88%; H-3.26%; N-31.96%

EXAMPLE 17

11-Oxo-11-H-pyrido[2,1-b]quinazoline-2-hydroxamic acid 5.9 gm of 11-oxo-11-H-pyrido[2,1-b]quinazoline-2-carboxylic acid chloride (see Example 12) were introduced into a solution of 2.08 gm of hydroxylamine hydrochloride and 9.8 ml of diisopropylamine in 100 ml of dimethylformamide, and the mixture was stirred at 20° C for 5 hours. Thereafter, the reaction mixture was acidified with dilute acetic acid and suction-filtered, yielding as the filter cake the semihyrate of the formula

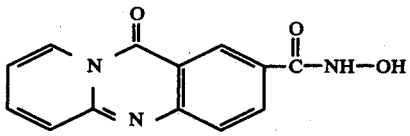

Elemental analysis: $C_{13}H_9N_3O \cdot 1/2H_2O$ Calculated: C-59.09%; H-3.79%; N-15.91% Found: C-59.20%; H-3.70%; N-15.49%

EXAMPLE 18

12-Oxo-12-H-quino[2,1-b]quinazoline-10-carboxylic acid 2.8 gm of ethyl 12-oxo-12-H-quino[2,1-b]quinazoline-10-carboxylate (see Example 3) were refluxed in 20 ml of an aqueous 10% sodium hydroxide solution for 30 minutes. The solution was then heated with 5 times its quantity of semiconcentrated hydrochloric acid for half an hour on a boiling water bath. After diluting with water, the precipitated yellow crystals were collected by suction filtration and washed with water and acetonitrile, yielding the compound of the formula

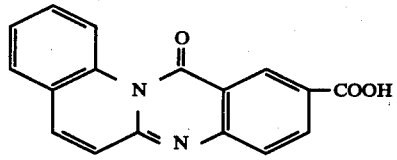

Elemental analysis: $C_{17}H_{10}N_2O_3$ Calculated: C-70.34%; H-3.45%; N-9.66%; O-16.55% Found: C-70.23%; H-3.50%; N-9.53%; O-17.02%

In like manner, and in analogy to Examples 12–18, the following additional compounds of the formula I were prepared:

Ethyl 5-oxo-5-H-thiazolo[2,3-b]quinazoline-7-carboxylate;
Ethyl 8-oxo-8-H-isoquino[1,2-b]quinazoline-10-carboxylate;
Ethyl 12-oxo-12-H-quino[2,1-b]quinazoline-10-carboxylate;
1-oxo-11-H-2-methyl-pyrido[2,1-b]quinazoline-8-carboxylic acid;
3-oxo-13-H-benzo[g]-pyrido[2,1-b]quinazoline-10-carboxylic acid;
1-oxo-11-H-2-methoxy-pyrido[2,1-b]quinazoline-8-carboxylic acid;
1-oxo-11-H-pyrido[2,1-b]quinazoline-3-carboxylic acid;
-oxo-6-H-pyrimido[2,1-b]quinazoline-8-carboxylic acid;
-oxo-5-H-thiazolo[2,3-b]quinazoline-7-carboxylic acid;
-oxo-8-H-isoquino[1,2-b]quinazoline-10-carboxylic acid; and
1-oxo-11-H-pyrido[2,1-b]quinazoline-2,8-dicarboxylic acid.

EXAMPLE 19

3-Amino-11-N-11-oxopyrido-[2,1-b]quinazoline-2-carboxylic acid 3.4 gm of 8-acetamido-11-H-11-oxo-pyrido[2,1-b]quinazoline-2-carboxylic acid (see Example 10) were heated on a boiling water bath with 30 ml of a mixture of water and concentrated sulfuric acid (2:3) for 30 minutes. Then, the reaction mixture was diluted with water, cooled and suctionfiltered. The filter cake thus obtained was purified by dissolving it in a soda solution, re-precipitating it with glacial acetic acid, collecting it by suction filtration, and washing with acetonitrile and ether. The hydrate of the formula

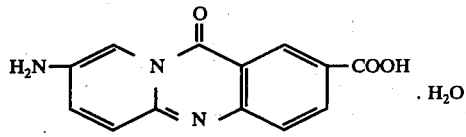

was obtained.

Elemental analysis: $C_{13}H_9N_3O_3 \cdot H_2O$ Calculated: C-57.14%; H-4.03%; N-15.38%; $H_2O$-6.6% Found: C-56.96%; H-4.09%; N-15.29%; $H_2O$-7.1%

The compounds of this invention, that is, those embraced by formula I above and salts thereof formed with acids or bases, have useful pharmacodynamic properties. More particularly, they exhibit primarily antiallergic activity, but also muscle-relaxing (bronchodilating) and vasodilating activities in warm-blooded animals, such as rats. The compounds are therefore useful for prophylaxis and treatment of various allergic disorders, such as asthma, hay fever, conjunctivitis, urticaria, eczema, atopic dermatitis and the like. When used for the prophylaxis of asthma, their most important utility, the principal advantage of the compounds of the present invention resides in their long duration of effective action and their peroral efficacy.

For pharmaceutical purposes the compounds of the present invention are administered to warm-blooded animals topically perorally, parenterally or by the pulmonary route as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, cremes, ointments, lotions, sprays and the like. The effective dosage depends upon the route of administration and the particular indication. For example, for administration by the pulmonary route the effective dosage range is about 20 to 500 μgm/kg body weight; for parenteral administration it is about 0.2 to 10 mgm/kg body weight; for oral administration it is about 1 to 50 mgm/kg body weight; and for nasal or ocular administration it is about 0.5 to 25 mgm/kg body weight.

The following examples illustrate a few pharmaceutical dosage unit compositions comprising a compound of the present invention as an active ingredient and represent the best modes contemplated of putting the invention into practical use. The part are parts by weight unless otherwise specified.

EXAMPLE 20

Tablets

The tablet composition is compounded from the following ingredients:

| | |
|---|---|
| 11-Oxo-11-H-pyrido[2,1-b]quinazoline-2-carboxylic acid | 0.100 parts |
| Stearic acid | 0.010 " |
| Glucose | 1.890 " |
| Total | 2.000 pats |

Preparation:

The ingredients are admixed and processed in conventional manner, and the composition is compressed into 2 gm-tablets, each of which contains 0.1 gm of the active ingredient.

EXAMPLE 21

Ointment

The ointment is compounded from the following ingredients:

| | |
|---|---|
| 13-Oxo-13-H-benzo[g]pyrido[2,1-b] quinazoline-10-carboxylic acid | 2.000 parts |
| Fuming hydrochloric acid | 0.011 parts |
| Sodium pyrosulfite | 0.050 parts |
| Mixture (1:1) of cetyl alcohol and stearyl alcohol | 20.000 part |
| White vaseline | 5.000 parts |
| Synthetic bergamot oil | 0.075 parts |
| Distilled water q.s.ad | 100.000 parts |

Preparation:

The ingredients are compounded in conventional manner, and the composition is processed into an ointment.

EXAMPLE 22

Inhalation aerosol

The aerosol composition is compounded from the following ingredients:

| | |
|---|---|
| Sodium salt of 11-oxo-11-H-pyrido[2,1-b] quinazoline-2-carboxylic acid | 1.00 parts |
| Soybean lecithin | 0.20 " |
| Propellant gas mixture (Frigen 11, 12 and 114) q.s.ad | 100.00 " |

Preparation:

The ingredients are admixed in conventional fashion, and the composition is charged into aerosol containers equipped with a metering valve which expells 5 mgm of the active ingredient with each actuation.

Any one of the other compounds of this invention may be substituted for the particular active ingredient in illustrative Examples 20–22, although the end products of Examples 1, 5 - 8 and 12 - 15 are particularly preferred as active ingredients. Likewise, the amount of active ingredient in these examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

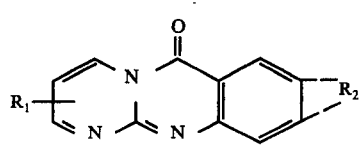

wherein $R_1$ is hydrogen, lower alkyl, lower alkoxy, amino, acetylamino, cyano, tetrazol-5-yl, —$COR_3$ or a fused benzene ring,
  where $R_3$ is lower alkoxy, amino, hydroxyamino, tetrazol-5-yl-amino or, when $R_2$ is other than hydrogen, also hydroxyl; and $R_2$ is cyano, tetrazol-5-yl, —$COR_4$ or, when $R_1$ is cyano, tetrazol-5-yl or —$COR_3$, also hydrogen, lower alkyl, lower alkoxy, amino, acetylamino or a fused benzene ring,
  where $R_4$ is lower alkoxy, amino, hydroxyl, hydroxy-amino or tetrazol-5-yl-amino;

a non-toxic, pharmacologically acceptable acid addition salt thereof; or, when $R_3$ and/or $R_4$ are hydroxyl, a non-toxic, pharmacologically acceptable salt thereof formed with an inorganic or organic base.

2. A compound of claim 1, which is 6-oxo-6H-pyrimido [2,1-b] quinaoline-8-carboxylic acid; a non-toxic, pharmacologically acceptable acid addition acid thereof; or a non-toxic, pharmacologically acceptable salt thereof formed with an inorganic or organic base.

3. The compound of claim 2, which is 6-oxo-6H-pyrimido [2,1-b]quinazoline-8-carboxylic acid.

4. The compound of claim 2, which is 6-oxo-6H-pyrimido [2,1-b] quinazoline-8-carboxylic acid hydrochloride.

5. The compound of claim 2 which, which is the sodium salt of 6-oxo-6H-pyrimido [2,1-b] quinazoline-8-carboxylic acid.

6. An antiallergic pharmaceutical composition consisting essentially of an inert pharmaceutical carrier and an effective antiallergic amount of a compound of claim 1.

7. The method of suppressing allergic reactions in warm-blooded animals, which comprises topically, perorally, parenterally or by the respiratory route administering to said animal an effective antiallergic amount of a compound of claim 1.

* * * * *

UNITED STATES PATENT OFFICE
CERTIFICATE OF CORRECTION

Patent No. 4,083,980           Dated    April 11, 1978

Inventor(s) KURT SCHROMM, ANTON MENTRUP, ERNST-OTTO RENTH and ARMIN FÜGNER

It is certified that error appears in the above-identified patent and that said Letters Patent are hereby corrected as shown below:

Col. 1, line 67, "expecially" should be --especially--

Col. 3, line 27, "compound" should be --compounds--.

In claim 2, line 3, "acid addition acid" should be

--acid addition salt--

Signed and Sealed this

Second Day of July 1985

[SEAL]

Attest:

DONALD J. QUIGG

Attesting Officer      Acting Commissioner of Patents and Trademarks